United States Patent [19]

Selenke

[11] Patent Number: 4,654,325
[45] Date of Patent: Mar. 31, 1987

[54] MEDICAMENT FOR REDUCING NEPHROTOXICITY CAUSED BY POSITIVELY CHARGED AGENTS SUCH AS AMINOGLYCOSIDES AND METHODS OF USE THEREOF

[76] Inventor: William M. Selenke, 18 Gambier Cir., Cincinnati, Ohio 45218

[21] Appl. No.: 613,876

[22] Filed: May 24, 1984

[51] Int. Cl.$^4$ .............................................. A61K 35/23
[52] U.S. Cl. ............................................................ 514/42
[58] Field of Search ..................... 260/112 R; 536/51; 525/54.11; 514/42

[56] References Cited

U.S. PATENT DOCUMENTS

| | | | |
|---|---|---|---|
| 3,900,398 | 8/1975 | Gillette | 210/196 |
| 4,199,570 | 4/1980 | Igarashi et al. | 434/180 |
| 4,200,628 | 4/1980 | Igarashi et al. | 424/180 |
| 4,201,774 | 5/1980 | Igarashi et al. | 434/180 |
| 4,226,747 | 10/1980 | Ronchri | 525/54.11 |
| 4,248,865 | 2/1981 | Igarashi et al. | 434/180 |
| 4,264,766 | 4/1981 | Fischer | 536/51 |
| 4,273,923 | 6/1981 | Igarashi et al. | 536/10 |
| 4,291,692 | 9/1981 | Bowman et al. | 128/214 E |
| 4,315,907 | 2/1982 | Fridlender et al. | 434/1 |
| 4,323,496 | 4/1982 | Mitani | 260/112 R |
| 4,335,114 | 6/1982 | Voss et al. | 434/180 |
| 4,362,710 | 12/1982 | Watanabe | 434/14 |
| 4,393,051 | 7/1983 | Stadler et al. | 434/180 |
| 4,423,210 | 12/1983 | McAlpine et al. | 536/16.1 |
| 4,427,662 | 1/1984 | Tadanier et al. | 434/180 |
| 4,430,433 | 2/1984 | Hammond et al. | 435/228 |
| 4,457,865 | 7/1984 | Miller | 260/112 R |

OTHER PUBLICATIONS

Polin, D. et al.: Amprolium 10. Influence of Egg Yolk Thiamine Concentration on Chick Embryo Mortality. Pro. Soc Exp. Bio. Med. vol. 110:844–846 (1962).

Besseghir, L. and Rennick, B. et al.: Renal Tubular Transport and Electrolyte Effects of Amiloride in the Chicken, Journal of Pharmacology and Experimental Therapeutics. vol. 219 (2):435–441 (1981).

Bennett, W. M. et al.: Effect of Basic Amino Acids in Aminoglycosides on $^3$H–Gentamicin Uptake in Cortical Slices of Rat and Human Kidney, Journal of Laboratory and Clinical Medicine, vol. 99 (2):156–162 (Feb. 1982).

Beyer, K. H. et al.: Functional Characteristics of the Renal Tubular Secretion of Amprolium, A Quaternary Organic Base, The Journal of Pharmacology and Experimental Therapeutics, vol. 195:pp. 194–200 (1975).

Polin, D. et al.: In Vivo Absorption of Amprolium and its Competition with Thiamine, Pro. Soc. Exp. Bio. Med. vol. 114:273–277 (1963).

Polin, D. et al.: Amprolim v. Studies in Laying Chickens and Their Eggs, Journal of Nutrition, vol. 76 (1):59–67 (Jan. 1962).

Bennett, W. M. et al.: Reduction of Experimental Gentamicin Nephrotoxicity in Rats by Dietary Calcium Loading, Antimicrobial Agents and Chemotherapy, vol. 22 (3):508–512 (1982).

Francke, E. et al.: Nephrotoxicity of Aminoglycosides, Infections in Surgery, (Mar. 1983).

Primary Examiner—Delbert R. Phillips
Attorney, Agent, or Firm—Wood, Herron & Evans

[57] ABSTRACT

Novel medicaments and methods of use thereof are disclosed for reducing in a human or an animal nephrotoxic effects associated with positively charged molecules or agents. The positively charged molecules or agents may be endogenous or exogenous to the human or animal. Examples of endogenous positively charged molecules or agents include proteins or myoglobin, whereas exogenous positively charged molecules and agents may be pharmaceuticals, such as those derived from the aminoglycoside antibiotic family. The medicament comprises a positively charged (cationic) substance which is preferably substantially inert and substantially secreted by the proximal tubules of the kidney. An example of a positively charged (cationic) substance that is substantially inert is amprolium. In addition, the medicament may include a pharmaceutical, such as an aminoglycoside antibiotic for treating bacterial infection.

29 Claims, No Drawings

MEDICAMENT FOR REDUCING NEPHROTOXICITY CAUSED BY POSITIVELY CHARGED AGENTS SUCH AS AMINOGLYCOSIDES AND METHODS OF USE THEREOF

BACKGROUND OF THE INVENTION

Aminoglycoside antibiotics, such as gentamicins, kanamycins, streptomycins and tobramycins, are generally utilized as broad spectrum antimicrobials effective against, for example, gram-positive, gram-negative and acid-fast bacteria. Nonetheless, the aminoglycosides are used primarily to treat infections caused by gram-negative bacteria and, for instance, in combination with penicillins for the synergistic effects. As implied by the generic name for the family, all the aminoglycoside antibiotics contain aminosugars in glycosidic linkage. Further, the aminoglycosides are characterized as polycations, and their polarity is responsible for the pharmocokinetic properties shared by all members of the family.

The aminoglycoside antibiotics, however, are often associated with undesired side-effects such as nephrotoxicity and ototoxicity. The seriousness of these toxicities is a major limitation to their usefulness, and, unfortunately, the same spectrum of toxicity is shared by all members of the family. It has been estimated, as of March 1983, that about 3.2 million or more people receive aminoglycoside therapy each year. Of those people receiving treatment, from about 2% to about 10% suffer clinical nephrotoxicity, as defined as an increase in serum creatinine of at least 0.4 mg/dl or onset acute renal failure. Thusly, the mechanisms and predisposing factors of aminoglycoside nephrotoxicity is critical in any attempt to minimize risk of therapy with these pharmaceuticals. Francke E. et al: Nephrotoxicity of Aminoglycosides. *Infections in Surgery*. Pages 204–214 (March 1983). In the past, it has been found that the toxic properties of many of the aminoglycoside antibiotics can be altered or reduced by structural modifications as described in U.S. Pat. No. 4,393,051 issued July 12, 1983 to P. Stadler et al.; U.S. Pat. No. 4,273,923, issued June 16, 1981 to K. Igarashi et al.; U.S. Pat. No. 4,248,865, issued Feb. 3, 1981 to K. Igarashi et al.; U.S. Pat. No. 4,201,774 issued May 6, 1982 to K. Igarashi et al.; U.S. Pat. No. 4,200,628, issued Apr. 29, 1980 to K. Igarashi et al.; and U.S. Pat. No. 4,199,570 issued Apr. 22, 1980 to K. Igarashi et al. In particular, it has been disclosed in U.S. Pat. Nos. 4,427,662 and 4,423,210, issued Jan. 24, 1984 to J. S. Tadanier et al. and Dec. 27, 1983 to J. B. McAlpine et al., respectively, that certain chemical modifications in the fortimicin, kanamycin and gentamicin family of aminoglycoside antibiotics provide structures which are less toxic than the parent antibiotics. Further, U.S. Pat. No. 4,335,114 issued June 15, 1982 to E. Voss et al. discloses derivatives of the aminoglycoside antibiotic sisomicin which avoid or reduce the undesired abovementioned toxicities.

Also, it has been found through testing in rats that dietary calcium loading reduces experimental gentamicin nephrotoxicity. More particularly, the effects of dietary calcium loading delay or attenuate gentamicin-mediated renal dysfunction and structural damage in Fischer line 344 rats. Since in vitro gentamicin uptake by rat renal cortical slices incubated in Cross and Taggart medium was reduced by calcium, it is postulated that the protection afforded with dietary calcium loading may be associated with slower renal cortical accumulation of gentamicin possibly mediated by calcium-dependent membrane or intracellular events. W. M. Bennett et al.: Reduction of the Experimental Gentamicin Nephrotoxicity in Rats by Dietary Calcium Loading. *Antimicrobial Agents in Chemotherapy*. 22(3): 508–512 (September 1982).

Amprolium [1-(4-amino-2-n-propyl-5-pyrimidinylethyl)2-picolinium chloride.hydrochloride], also known as amiloride, is a coccidostat presently used in veterinary medicine. It is a weak anti-metabolite of thiamine which is capable of producing thiamine deficiency in chicks, adult chickens and eggs. Administration of thiamine, however, overcomes the vitamin deficiency. Notwithstanding this shortcoming, amprolium is quite non-toxic and is allowed as a residue in eggs for human consumption when it is given to chickens. Amprolium is one of the few positively charged (cationic) compounds that is secreted by the proximal tubular system of the kidneys which has minimal biological and/or pharmacological activity. Generally, the majority of positively charged compounds are very active biologically and pharmacologically and, therefore, can only be given in small doses. An example of a positively charged compound which is well-known, very pharmacologically active and secreted by the proximal tubules is nicotine.

It is generally accepted today that positively charged (cationic) molecules induce nephrotoxicity. For instance, proteins having an increased isoelectric point, like Bence Jones proteins, are thought to cause kidney damage in part by inhibition of proteolytic enzyme activity. The predisposing factors by which positively charged molecules, such as aminoglycosides and Bence Jones proteins, induce nephrotoxicity are believed to be due to their filtration through the glomerula membrane, their binding to the membranes of the proximal tubule cells and their accumulation within the proximal tubule cells of the kidney. As to aminoglycosides, it is believed that absorption occurs exclusively along the proximal tubules and Henley's Loop and that pinocytosis is the major mechanism of aminoglycoside entry into the proximal tubule cells. Once inside the proximal tubule cells, it is postulated that the pathophysiology and epidemiology associated with the nephrotoxicity of these drugs is due to their ability to disrupt lysosomal function and/or release active unhibited lysosomal enzymes. E. Francke et al.: Nephrotoxicity of Aminoglycosides. *Infections in Surgery*. Pages 205–214 (March 1983).

In other words, positively charged molecules, and especially the most popular and commonly used aminoglycoside antibiotics provided hitherto invariably necessarily induce undesired nephrotoxic effects. Consequently, there are strong medical needs for developing a pharmaceutical substance and/or a course of therapy that will reduce the nephrotoxicity presently associated with positively charged molecules, and particularly the commonly used aminoglycosides.

SUMMARY OF THE INVENTION

In brief, the present invention seeks to alleviate the above mentioned problems and shortcomings of the present state of the art through the discovery of a novel course of therapy and the use of a novel medicament for reducing nephrotoxicity presently associated with positively charged molecules, and particularly the commonly used aminoglycosides. The new and vastly improved medicaments and methods of use thereof comprises administering into a human or animal a positively charged (cationic) substance which is secreted by the proximal tubules of the kidney in a pharmaceutically accepted carrier for reducing the nephrotoxic effects associated with such positively charged agent. If the nephrotoxic causing agent is exogenous to the human or animal, such as an aminoglycoside antibiotic, the positively charged (cationic) substance of this invention may be administered at a suitable interval(s) either prior or subsequent to, or substantially concurrently with the administration of the exogenous agent. Preferably, the positively charged (cationic) substance is substantially inert, such as amprolium or any suitable derivative thereof. The nephrotoxic causing positively charged molecules or agents on the other hand may be, for instance, a pharmaceutical, a protein or myoglobin. In addition, the positively charged (cationic) substances of this invention may be employed to reduce nephrotoxicity currently associated with positively charged molecules or agents, such as proteins, which are endogenous to a human or other types of animals.

Further, the present invention is directed to a medicament comprising a positively charged pharmaceutical agent for administering into a human or animal which induces nephrotoxicities and a substantially inert positively charged (cationic) substance in an amount effective to reduce the nephrotoxic effects caused by the positively charged agent.

Still further, the invention relates to the use in medicine of medicaments of the invention in cases of bacterial infection. Thusly, the present invention provides a solution to the art that has long sought a therapy and a medicament which can reduce the nephrotoxic effects currently associated with positively charged molecules or agents and in particular the more popular and commonly used aminoglycoside antibiotics without sacrificing the antimicrobial effectiveness of the aminoglycosides.

DETAILED DESCRIPTION OF THE INVENTION

By way of illustrating and providing a better appreciation of the present invention, the following detailed description is given concerning the medicament of the invention and methods of use thereof.

In accordance with the present invention, it is directed to providing pharmaceutical substances and methods of use thereof for reducing in a human or other species of an animal nephrotoxicity induced by positively charged molecules or agents. This is accomplished in the present instance by means of administering in an effective amount to a human or animal a pharmaceutical substance which is positively charged and secreted by the proximal tubules of the kidney. To this end, it is not necessary, but highly preferable, that the positively charged substances be substantially inert. By "substantially inert", it is meant that the positively charged substances exhibit minimal biological and/or pharmacological activity. The following substantially inert positively charged substances used according to the teachings of the invention and mentioned by way of illustration are preferably amprolium or any suitable derivatives thereof. Amprolium is especially advantageous and uniquely suited for application in accordance with this invention because it is a cationic substance, it is substantially inert and it is substantially secreted by the proximal tubules of the kidney.

This invention further provides that the positively charged molecules or agents which induce nephrotoxicity may be exogenous or endogenous to a human or animal. For instance, examples of endogenous agents include, but not limited to, positively charged proteins, such as Bence Jones proteins, and myoglobin. Whereas examples of exogenous agents are those derived from the aminoglycoside family.

In addition to the positively charged (cationic) substances of the invention, the pharmaceutical compositions and medicaments according to the invention can also contain other pharmaceutical molecules or agents. They may also contain a plurality of substances of the invention. The pharmaceutically active molecules or agents may be positively charged which induced nephrotoxicity, such as aminoglycoside antibiotics. Preferably the aminoglycoside antimicrobials are selected from the class consisting of amikacin, dibekacin, fortimicin, gentamicin, kanamycin, netilmicin, neomycin, paromomycin, sisomicin, streptomycin or tobramycin.

In forming a medicament according to the invention may, for example, comprise a substantially inert positively charged (cationic) substance which is renally secreted by the proximal tubules, such as amprolium, and, for instance, an aminoglycoside antibiotic wherein each are in effective amounts. An important advantage of the use, according to the invention of the combination of, for example, amprolium and an aminoglycoside antibiotic is to provide a medicament for convenient concurrent administration. It should be understood, however, that a medicament containing, for instance, amprolium and a medicament containing an aminoglycoside antibiotic may also be given concurrently without departing from the scope of the invention. Such a course of therapy employing the combined pharmaceutical medicaments now affords the medical community with an opportunity heretofore unavailable to treat bacterial states in a human or animal with aminoglycoside therapy while reducing the nephrotoxicity presently associated with such therapy.

In the specification, the term "medicament" refers to physically discrete, coherent portions suitable for medical administration. The medicament may of course be in a dosage unit form which is a discrete coherent unit suitable for medicinal administration containing a daily dose or a multiple or sub multiple of a daily dose of, for instance, amprolium combined, if necessary, with a suitable pharmaceutical carrier or vehicle. Whether the medicament contains a daily dose or, for example, a half, a third or a quarter of a daily dose will depend upon whether the medicament is to be administered once, or, for instance, twice, three times or four times a day respectively.

It is envisaged that the positively charged (cationic) substance, such as amprolium, may be administered by a suitable route concurrently with other pharmaceuticals as noted above, or prior or subsequent to the administration of the pharmaceutical. It is preferred, however, to administer a suitable amount of the positively charged substance in, for example, a loading dose or doses prior to the administration of a positively charged pharmaceutical which induces nephrotoxicity for reducing such undesired effects.

As already noted, the positively charged (cationic) substances and methods of use thereof are suitable for reducing in humans or animals nephrotoxic effects experienced with positively charged molecules or agents. In accomplishing the above, it is believed that since the positively charged substances of this invention are secreted by the proximal tubules of the kidney, a net positive charge is "forced" through the proximal tubular cells. Thus, it is thought that the positively charged substances reduce the nephrotoxic effects induced by positively charged molecules or agents by inhibiting or interfering with the uptake of such positively charged molecules or agents and by repelling or forcing out such positively charged molecules or agents present in the proximal tubular cells of the kidney. For example, the positively charged substances of this invention and methods of use thereof may inhibit the uptake and/or force out of the proximal tubule cells of the kidney positively charged proteins, such as Bence Jones proteins, or pharmaceuticals, like aminoglycoside antibiotics, for reducing the undesired nephrotoxic effects associated therewith. It should be understood, however, that the above set forth mechanism of action is for illustrative purposes only and it is not intended to limit the invention to any specific theory or mechanism by which the nephrotoxic effects associated with the positively charged molecules or agents are reduced in accordance with the teachings of this invention.

The present invention may, of course, be carried out in other specific ways than those herein set forth without departing from the spirit and essential characteristics of the invention. The present embodiments are, therefore, to be considered in all respects as illustrative and not restrictive and any changes coming within the meaning and equivalency range of the appended claims are to be embraced therein.

What is claimed is:

1. A medicament for reducing in an animal nephrotioxic effects caused by an aminoglycoside comprising an effective amount of a cationic substance which is substantially secreted by proximal tubules of kidney in a pharmaceutically accepted carrier for reducing the nephrotoxic effects caused by the aminoglycoside.

2. A medicament of claim 1 wherein the cationic substance is substantially inert.

3. A medicament of claim 1 wherein said cationic substance is amprolium.

4. A medicament of claim 1 wherein the aminoglycoside is selected from the class consisting of amikacin, dibekacin, fortimicin, gentamicin, kanamycin, netilmicin, neoomycin, paramomycin, sisomicin, streptomycin or tobramycin.

5. A medicament of claim 1 wherein the medicament further comprises an aminoglycoside in a dose effective for treating a bacterial infection.

6. A medicament of claim 5 wherein the aminoglycoside is selected from the class consisting of amikacin, dibekacin, fortimicin, gentamicin, kanamycin, netilmicin, neomycin, paramomycin, sisomicin, streptomycin or tobramycin.

7. A medicament of claim 5 wherein the cationic substance is amprolium.

8. A method of reducing in an animal nephrotoxic effects caused by an aminoglycoside comprising
administering to an animal a medicament comprising an effective amount of a cationic substance which is substantially secreted by proximal tubules of kidney in a pharmaceutically accepted carrier for reducing the nephrotoxic effects caused by the aminoglycoside.

9. A method of claim 8 wherein the cationic substance is substantially inert.

10. A method of claim 8 further comprising the step of administering an aminoglycoside in an effective amount for treating a bacterial infection wherein the cationic substance is administered at a suitable interval which precedes or succeeds said administration of the aminoglycoside.

11. A method of claim 8 further comprising the step of administering an aminoglycoside in an effective amount for treating a bacterial infection wherein the cationic substance is administered substantially currently with the administration of the aminoglycoside.

12. A method of claim 8 wherein the medicament further comprises an aminoglycoside in an effective amount for treating bacterial infection.

13. A method of claim 12 wherein the aminoglycoside is selected from the class consisting of amikacin, dibekacin, fortimicin, gentamicin, kanamycin, netilmicin, neomycin, paramomycin, sisomicin, streptomycin or tobramycin.

14. A method of claim 8 wherein the cationic substance is amprolium.

15. A method of claim 12 wherein the cationic substance is amprolium.

16. A medicament for reducing in an animal nephrotoxic effects caused by myoglobin or Bence Jones proteins comprising an effective amount of a cationic substance which is substantially secreted by proximal tubules of kidney in a pharmaceutically accepted carrier for reducing the nephrotoxic effects caused by the myoglobing or Bence Jones proteins.

17. A medicament of claim 16 wherein the cationic substance is substantially inert.

18. A medicament of claim 16 wherein the inert cationic substance is amprolium.

19. A method of reducing in an animal nephrotoxic effects caused by myoglobin or Bence Jones proteins comprising
administering to an animal a medicament comprising an effective amount of a cationic substance which is substantially secreted by proximal tubules of kidney in a pharmaceutically accepted carrier for reducing the nephrotoxic effects caused by the myoglobin or Bence Jones proteins.

20. A medicament of claim 19 wherein the cationic sustance is substantially inert.

21. A method of claim 19 wherein the inert cationic substance is amprolium.

22. A medicament for reducing nephrotoxic effects associated with an aminoglycoside, myoglobin or Bence Jones proteing comprising
an effective amount of amprolium in a pharmaceutically accepted carrier for reducing the nephrotoxic effects associated with the aminoglycosde, myoglobin or Bence Jones protein.

23. A medicament of claim 22 wherein the aminoglycoside is selected from the class consisting of amikacin, dibekacin, fortimicin, gentamicin, kanamycin, netilmicin, neomycin, paramomycin, sisomicin, streptomycin or tobramycin.

24. A method of reducing in an animal nephrotoxic effects caused by an aminoglycoside, myoglobin or Bence Jones proteins comprising
administering to an animal a medicament comprising an effective amount of amprolium in a pharmaceutically accepted carrier for reducing the nephrotoxic effects caused by the aminoglycoside, myoglobin or Bence Jones proteins.

25. A method of claim 24 wherein the aminoglycoside antibiotic is selected from the class consisting of amikacin, dibekacin, fortimicin, gentamicin, kanamycin, netilmicin, neomycin, paramomycin, sisomicin, streptomycin or tobramycin.

26. A medicament for reducing nephrotoxic effects caused by a positively charge substance comprising an effective amount of amprolium in a pharmaceutically accepted carrier for reducing the nephrotoxic effects caused by the positively charged substance.

27. A medicament of claim 26 wherein the postively charged substance is secreted by the proximal tubules of the kidney.

28. A method of reducing in an animal nephrotoxic effects caused by a positively charged substance comprising
adminsistering to the animal a medicament comprising an effective amount of amprolium in a pharmacuetically accepted carrier for reducing the nephrotoxic effects caused by the positively charged agents.

29. A method of claim 28 wherein the positively charged substance is secreted by the proximal tubules of the kidney.

* * * * *